United States Patent [19]
Wallach et al.

[11] Patent Number: 5,959,094
[45] Date of Patent: Sep. 28, 1999

[54] P75 TNF RECEPTOR PROMOTERS

[75] Inventors: David Wallach, Rehovot, Israel; Peter Kuhnert, Berne, Switzerland; Gotz Ehrhardt, Steisslingen, Germany; Oliver Kemper, Bockenheim, Germany

[73] Assignee: Yeda Research and Development Co. Ltd., Rehovot, Israel

[21] Appl. No.: 08/737,371

[22] PCT Filed: May 11, 1995

[86] PCT No.: PCT/US95/05853

§ 371 Date: Nov. 12, 1996

§ 102(e) Date: Nov. 12, 1996

[87] PCT Pub. No.: WO95/31206

PCT Pub. Date: Nov. 23, 1995

[30] Foreign Application Priority Data

May 11, 1994 [IL] Israel ........................................ 109633

[51] Int. Cl.⁶ .................................................. C12N 15/11
[52] U.S. Cl. .......................................................... 536/24.1
[58] Field of Search .............................. 536/24.1; 514/44

[56] References Cited

PUBLICATIONS

Orkin et al, Report and Recommendations of the Panel to Assess the NIH Investment in Research On Gene Therapy, NIH, published Dec. 7, 1995, various unnumbered pages.
Kadonaga, James T. et al., "Affinity purification of sequence-specific DNA binding proteins.", Proc. Natl. Acad. Sci., vol. 83, pp. 5889–5893 (Aug. 1986).
Bielinska, Anna et al., "Regulation of gene expression with double–stranded phosphorotioate oligonucleotides.", Science, vol. 250, pp. 997–1000 (Nov. 16, 1990).
Mitchell, Pamela J. et al., "Transcriptional regulation in mammalian cells by sequence–specific DNA binding proteins.", Science, vol. 245, pp. 371–378 (Jul. 28, 1989).
Singh, Harinder et al., "Molecular cloning of sequence–specific DNA binding proteins using recognition site probes.", Biotechniques, vol. 7, No. 3, pp. 252–261 (1989).
Kemper, Oliver et al., "Cloning and partial characterization of the promoter for the human p55 tumor necrosis factor (TNF) receptor.", Gene, vol. 134, pp. 209–216 (1993).
Rothe, Joachim et al., "Genomic organization and promoter function of the murine tumor necrosis factor receptor B gene.", Molecular Immunology, vol. 30, No. 2, pp. 165–175 (1993).
Smith, Craig A. et al., "A receptor for tumor necrosis factor defines an unusual family of cellular and viral proteins.", Science, vol. 248, pp. 1019–1023 (May 25, 1990).
Kohno et al., "A second tumor necrosis factor receptor gene product can shed a naturally occurring tumor necrosis factor inhibitor.", Proc. Natl. Acad. Sci., vol. 87, pp. 8331–8335 (Nov. 1990).
Kuhnert et al (1994). "Cloning, sequencing and partial functional characterization of the 5' region of the human p75 tumor necrosis factor receptor–encoding gene (TNF–R)". Gene, vol. 150, pp. 381–386.

Primary Examiner—Terry McKelvey
Attorney, Agent, or Firm—Browdy and Neimark

[57] ABSTRACT

The present invention is an isolated DNA molecule comprising a promoter of the human p75 TNF-R gene having a sequence consisting of a 5' upstream promoter sequence contained within an approximately 2.0 kbp NcoI fragment of a genomic clone of human p75 TNF-R, or an intron promoter sequence located in the first intron between the first and second exons and contained within an approximately 1.9 kbp SmaI fragment of a genomic clone of human p75 TNF-R. A composition comprising the DNA molecule and a carrier is also described.

4 Claims, 4 Drawing Sheets

FIG. 2a

```
   1  CCATGGAACAC TG TGCCCT T TCC T TCCCAAACCCTCACCCCTGGGCCTGACCCTGGAG TCAAGAACTGCAC TTGGCAGAG TT CAGAGAGAAGTCGCCTGC
                                             NF-kB                                                       NF-kB
 101  TCTCAAGCC TGGGTCGGCC T GGA G AAGGGGAGAAGCCCCATG TTGCATAGAAGA TTAAGC TTGAA TTCG TTCCCAGGATGGGACCTAAGCCTGGGAGGATC
 201  CCCACC TTCAGGAGGTGATG G TGC C ATTCACTGGGATAGGAAACTGGCAGGAGGAGCCGG TTG TTGAGGG TTGGGGGTGCAGACAGTCTG TTGGTCCA
 301  T TGGTC TTGAGGTGTG TGGGGGACAAC TAGAGAGAACTA TTG TCCCCTGC TTCCACGAGGTGACA TCTCCC TCCTGCC TTCAGCTCTA TT TTAGGGATCA
 401  AGGAG TCC TTGGAGC TGC TCCTAGGCA TTCTCA TAAGGGCCAGAAGAGC TCTGCATGTCTGTCCAGGGCTCTGCAGAG TTAAGGC TGTGGGTCATACCA
                                                                                                   NF-kB
 501  GCCACACCC TCAGCG TGGTCCA TGTCACAGAAACA TGTGGAAACCAGGTGA TTTCCCAGCCTCC TGGTCAGGAGGTGGGG TT TTCCATCCCAGGAGTC
      IFN
 601  AC TTCCCAG TTTC TCACTCAGCACTCAGAAGCACCATCC TTGCAGGCTCCAC TGTGGGGC TGGTGGCCGGGAGAAAGG TC TCTGTACC TCTT
                                                                                TATA - box
 701  CAGGCAGCCTGCAG TGAGGAAACAGGGAACAGAA TAGCCTCC TGCCACCCAGCCCACCCCAACCC TTAGAAA TGCCCTA TGTGCTGGGGGCTAGGACCCC
 801  CGTAA TCCAGGGCTGGGAGGAA TGTGC TCTGGCCCCCGCAGGGCTGCCC TGTA TTAGGGCTGCACTCAAAGTGGGATGGGGGACAGA TTGCAGCTGGA
      Octamer
 901  ATGGG TGCTCGG TGATGATGTAAATCCTGGCGAAGCCAGC TCTCCTGGCCTGG TCTCACCAGCCCCTCAGGGCCTGCAGC TTCCC TGGTGACA TTCTC
1001  TCCCAGCC TCTG TTCATCTGCCCCCTGCCCTGGGCAGGAGAC TTGAGCAGGGAAG TGCAGAG TC TTC TCCCTGTGAGAAGGC TGGATGCGTG TTAAGGAT
                                                                                        TATA - box
1101  AAATGAACACGCGAAGAG TAGTAACAACAGCCAAGA TT TATAAATGCC TATTG T TA TA TA TGTAGATAC T TAC T TAAG TATA TATAAAG TACAGACTGCA
                                    p sequence
1201  T TATG TATA TTACA TATC TTT AAATTT T TAG AA TAG TCCTA TGAGGTCAGTTCA GA GATC CAGACCCAGGTGGTCTGCTCTAGAGTCTAAACAGGCCGA
                                  TATA - box                                      IFN
1301  GTGCAGTGGCTCACACCTATAATCCCAGCACCCTTGGGAGGCCAGAGGCGGGAAGATCAC TTGAGGG TGGGAAGAACACG TGAGCTCAGGAG TT CGAGACC
1401  AGCCTGGACAACATGGCGAAACCCA TCTC TATAAAGAAATCAGCTAGCATGGTGGCCCGAGCCT GTAGTCCCAGCT ACTCGGGGAGGCTG AGG TGGGAG
                                    TATA - box
1501  GATCGCTTGAGCGCGAGGAG TTGGAGGC TGCAGTGAGCTATGGTGAAAGAGTGAGACCTTGTCTCA AAAAAAA TTAAA AAA TAAGA A TTAAA TA T A TTTA
      IFN                                                                                                    HMGI
1601  AAA TAGAG TCTAAATAAGT GA ATGA TCTAGAA TTCTC TTGGTTCCCCTAAAGCAGCTGTCAGC TT TGGGGGATG TTT TTCCAAA TTAG TGCC TCACCCTC
1701  ACGGGACAGGAGAAGCCTGTGGGAGCTGGGAGGCAGGTGGAGGCCGGGCAGGTGGAGGGCGCGAGGGCGCGAGGGCAACCGGGCAGGGGCAACCGACCCCGCCACCCATGGCGC
                              kappa-E2                                   kappa-E2           CK-1
1801  GGAGGAGGTTGAGGGGTCACCCAGGTGCTGGAGTGACGCTGGAGTATCGGCCCAGCGATGCTGGAGTGGTCGGGTCGGAGGCCCAGCAGCGTCTGGGG
      YY1         SP-1   (ETF)
1901  AGGGGCGTGGGGGAGGCGTGTCCAAGGCCGGGCAGGGGCCGCCCCCGCCGGGGCTGCCCCTGGCCCTGGAGGGCGCGAGGGCGCGGCTTTCGCTTTCAGTCGAGG
                                                                                         F6 (IRF-1)
2001  GCTAGCGAGCGCAGCGGAGCCTGGAGAGAGAAAGGCGCTGGGCTGCGAGGGCGCGAGGGCGCAACCGGGCAGGGGCAACCCCGCCACCCATGGCGC
                                                                                GC - box             Met Ala P
      ro Val Ala Val Trp Ala Ala Leu Ala Val Gly Leu Glu Leu Trp Ala Ala His Ala Ala Leu Pro Ala Gln
2101  CCGTCGCCGTCTGGGCCGCGCTGGCCGTCGGACTCGAGCTCTGGGCCGCGCACGCGCCCTTGCCGCCCAGGTGGTGACT
                                                                  5' splice site
```

FIG. 2b

```
1     CCCGGGGGTCCTGGGAAGGCACAATGGTGACAGTGCTGCAGCTCCTGAGGGTCACTCAGAGACCCGAGAGAGAGGGCTCTGCGTCTGCTCC

101   TCTG TCCAGGGCTGTAGCTTC TCTGGGTGCCTTTGCTT TCTCTT TTCTCCCCT CTT TTTTT TTT TT TTCGAGATGGA GTT TTGCTCTGT CAATTAGGC
                                              TCC repeat                              NF-kB                      CK-1

201   TGGAAGTGC AGTGGCATGAT TCAGCTCACTGCAACCTCCTCCTCCCAGGTTCAGGGGATTCTCCTGCCTCAGCCTCCAGAGTAGCTGGGA TTACAGGCA
                                                                                                          IFN

301   CA CGCCACTA TGCCGGATAATT TTGTA TTTT TAGTAGAGACAGGGTTTTGCCT TGTTGGCCAGGCTGGTCTCGAACTCTTGACCTC AAGTGATCCACCT
                                                                                                  CK-1

401   GCT TCGGCCTCCCAAAGTGC TGGGATTACAGGTGTGAGCCACCACACCTGGCCCTCTCTCTT TTCA TTCATCACATTG TTCATCTCTTCCCGGAGGCA
                                                                                                          IFN

501   TCCA GCACAGTC TTTGAGAC TGTGAGCTGTGAAGTCAGACAGAGGACCCAGGTCCAAACCCTTCTCTGTCACTTACCAGGTCTGGGACCTTGGGCAGGTGAC
                 TATA - box                                            YY1, CAP - site 601   CTGCCCTCTCAGGCCTCGG T T TCCTGTTCTATAAA ATGGCTGCAGTAGGGAAACCGTCTCCATCTTCATTGGGTGGTTGGGAAGTCTTGCTGAGACCACA
           CK-2                                                                        IFN 701   CACCTGTCTCAGGTAGGG TCTTCCAGAAGCAGAGC CTGAGGCAGGATCTTT GTGAAAGTGATTTGCTAGGGAGGGCTCCCAGGAGAAGCAGGCAGGGCA 801   GGTCAGGGGAGGGGGCTTAGCAGGGACGTTGTTCACCAGCTTCAGCCAGCTCTGGACCATGAATTGTACCAGGGTGGGTCCCACC 901   TTGAGGCTGTGGAGCATTCATTATCAGCCAACACCCCACAGCTGGGGAGCCCTGCCTGCTGGCAGCAGGGTCTGAGTGGGGTGCAACAGCACCCA 1001  CCAATTCGAGCAGCAGAAAACGCTTAGAACAGTGCCTAGGCACCTGGTACCTAGCCAGTGCT TCAAAAA TGGCAACGAT TGTCATGGTCATAACCAACA T TCAGCTGAT 1101  GAGTGCCGGCTCTACGGTGGGTCCCATGTGAGAGATTGAGGGTCTAGAGATGACAAGGCTGCCACCTCTG CTGTCTGCATCACAAGT GTGTGTGTACACA 1201  TGTGTGTGCATACATACCCACAGGGGG TGGAACGACAAGCAAGTAACCATTCCAGAACAATGAGA TGACTG TTAGAGGGGTCATAACCCACGTT TAGAGA 1301  GAGCCAGAGGAGGAGGAGGAGGAGAGCTTGAATTAGCCTTGGGAGTGCAGGGAGGCTTCCCAGAGGAGGCAGCACTCATCTTGAAAGACAAAGGGATGTT
                       TCC repeat 1401  TCAGGTGCAGGAGGGAAGGAGAGG TATCTTCCTTCCTCAGCAGAAGGCAGCT TTGTGCTGAGAACCCCGTTCTCTGTGACCAAGGCCACTGTCTTCTGG 1501  ATATCTGTCCATGCAGTGTTAGGGTCACCCAGCACTGGAGAAGGCCAGCA GAGTCAGTGCTTCTGCCTGCAGACATGACTAGGGTACACTGAGGTGGG 1601  GAGGCAGGGGAGGTAAAAGAAGGCACGAGCTCTCCTTCCTGTCCCTGTACCCTCCCCAGGGGGAGAAACCTCCCCAGCCATCATCAGTGCAGACTGGCAGGGGGA
                                                                                                              Val Ala 1701  GGGCCAAACATTTGCAGGGCGGGGGACCTGGGACCTGAGCAGGCATGGCAGAACCCAGGGGCCGGCCCTGTTGATGGCAGTCTTCCCTCTTCCTTCCAGGTGGCA 1801  Phe Thr Pro Tyr Ala Pro Glu Pro Gly
      TTTACACCCTACGCCCCGAGCCCGGG
                           3' splice site
```

P75 TNF RECEPTOR PROMOTERS

CROSS-REFERENCE TO RELATED APPLICATIONS

This application is a 371 of PCT/US95/05853, filed May 11, 1995.

FIELD OF THE INVENTION

The present invention relates to a promoter sequence for the p75 tumor necrosis factor receptor (TNF-R), to its preparation and use.

BACKGROUND OF THE INVENTION

TNF is a multifunctional pro-inflammatory cytokine which affects a wide range of cellular functions. On the one hand, TNF is involved in the protection of the organism, but on the other hand, when over-produced, it can play a major pathogenic role in several diseases. TNF is known to be involved in inflammatory processes and to be a mediator of the damage to tissues in septic shock (1), graft-versus-host reactions (2) and in rheumatic diseases (3).

TNF exerts these effects by binding to two distinct cell surface receptors, which differ in size (about 55 and 75 kDa) and possess structurally dissimilar intracellular domains, suggesting that they signal differently (4–11). Almost all cells express TNF receptors (TNF-Rs), yet the amounts and relative proportions of the two receptors vary in different cell types. These variations are in part developmentally controlled; they are related to the phenotype of the cell and its state of differentiation, and in part can be induced transiently by cytokines and immune stimulatory components of pathogens (12–22). Studies of the function of the two TNF-Rs indicate that they have different yet interacting activities (23–28), and that their activity level may be correlated to the extent of their expression by the cell (29, 30). These findings imply that the mechanisms which affect the amounts and relative proportion of the two TNF-Rs can have significant influence both on the nature and the extent of the cellular response to TNF and thus constitute important determinants of the physiological as well as pathological manifestations of the function of this cytokine.

In order to inhibit the deleterious effects of TNF, ways were sought which would interfere with the binding of TNF to its receptors. Thus neutralizing antibodies to TNF were raised (EP 186 833). Another approach to the inhibition of the action of TNF was the provision of soluble TNF receptors which compete with the cell surface TNF-Rs for the binding of TNF (EP 308 378 and EP 398 327).

Since binding to its receptors is required for TNF in order to exert its action, if less or no cell surface receptors are expressed, it should be possible to decrease or inhibit the deleterious effects of TNF. By the same token, it may be desired in certain cases to augment the beneficial action of TNF and in such a case this could possibly be achieved by increasing the amount of cell surface receptors expressed.

SUMMARY OF THE INVENTION

The present invention provides a promoter sequence of the human p75 TNF-R gene selected from a sequence which is located upstream of the 5' end of the gene and a sequence which is located in the first intron of the gene. The 5' upstream promoter sequence (called the 5' region promoter sequence) is contained within a 2.1 kbp sequence, and the intron promoter sequence is contained within a 1.9 kbp sequence. The 5' region promoter sequence is capable of controlling the expression of the native p75 TNF-R gene product, while the intron region promoter sequence is capable of controlling the expression of a truncated p75 TNF-R gene product. Further, the intron region promoter may also function as an enhancer element for the transcription of the p75 TNF-R gene. Moreover, the intron region promoter has upstream to the intron promoter a transcription inhibitory region, which may serve as a modulator for the expression of the truncated p75 TNF-R gene product.

The invention in preferred embodiments provides the 2.18 kbp NcoI fragment, encoding the 5' region promoter sequence, and the 1.8 kbp SmaI fragment, encoding the intron promoter sequence, both fragments being derived from a genomic library containing the human p75 TNF-R. Other preferred embodiments provided by the invention are a portion of the 5' region promoter sequence containing the essential promoter activity and extending between at least nucleotides 1335 and 1527 of the sequence depicted in FIG. 2A; a portion of the intron promoter sequence containing the essential promoter activity and extending between at least nucleotides 1569 and 1768 or between at least nucleotides 1569 and 1827 of the sequence depicted in FIG. 2B; and a portion of the intron promoter region sequence containing the transcription inhibitory region and extending between nucleotides 1 and 1569 of the sequence depicted in FIG. 2B.

In another aspect, the invention provides sequence motifs present in the above described promoter sequences, including the promoters of the 5' upstream and intron regions as well as the transcription inhibitory region of the intron region. Such motifs have been shown to bind certain transcription factors which could be necessary for promoter activity and might be involved in regulation of this promoter.

The motifs may be prepared by deletion of the unwanted sequences upstream and/or downstream the desired motif in the full sequence, i.e. by employing restriction enzymes to cut the full promoter sequence to arrive at the desired motif, and the resulting motif can then be inserted into a vector together with suitable control sequences and other conventional means required in order to obtain a vector which, on insertion into a suitable prokaryotic strain is capable of expression of the desired motif on culturing of the strain.

The motif thus obtained can be used to screen, e.g. a human genomic library or a cDNA library for factors, e.g. transcription factors, binding thereto. Once these factors have been isolated, purified and identified by any conventional means, their inhibition should inhibit TNF-R formation, while their increased production should cause enhanced TNF-R expression thereby leading to the desired effects, i.e. inhibition or enhancement of TNF binding to its receptors.

Since the amount of specific transcription factors present in vivo is not unlimited, inhibition of TNF-R expression and, as a consequence, inhibition of deleterious TNF effects could also be achieved by the expression of a large number of motifs or motif regions. These will compete with promoters containing such motifs or motif regions for binding of the transcription factors. A "motif region" comprises the motif itself together with sequences flanking it on both sides, or several motifs connected by parts of the whole promoter sequence and flanked on both sides by sequence parts. It is to be understood that a motif or motif region according to the present invention, as noted above, and as set forth hereinbelow includes those present in both the active promoter regions and the transcription inhibitory region according to the invention. Likewise, the transcription factors of the invention include those which bind the active promoter regions and those which bind the transcription inhibitory region.

The present invention also provides pharmaceutical compositions comprising a sequence motif according to the invention.

In another aspect, the invention provides pharmaceutical compositions comprising a motif region according to the invention.

DESCRIPTION OF THE DRAWINGS

FIGS. 2A and 2B show, schematically, the nucleotide sequences of the 5' upstream promoter region and the coding sequence for an exon (FIG. 2A) (SEQ ID NO:1), with the amino acid sequence encoded by the exon (SEQ ID NO:2), and the nucleotide sequence of the intron promoter region and the coding sequence for another exon (FIG. 2B) (SEQ ID NO:3), with the amino acid sequence encoded by the exon (SEQ ID NO:4), as described in Example 2.

DETAILED DESCRIPTION OF THE INVENTION

Figure 1:
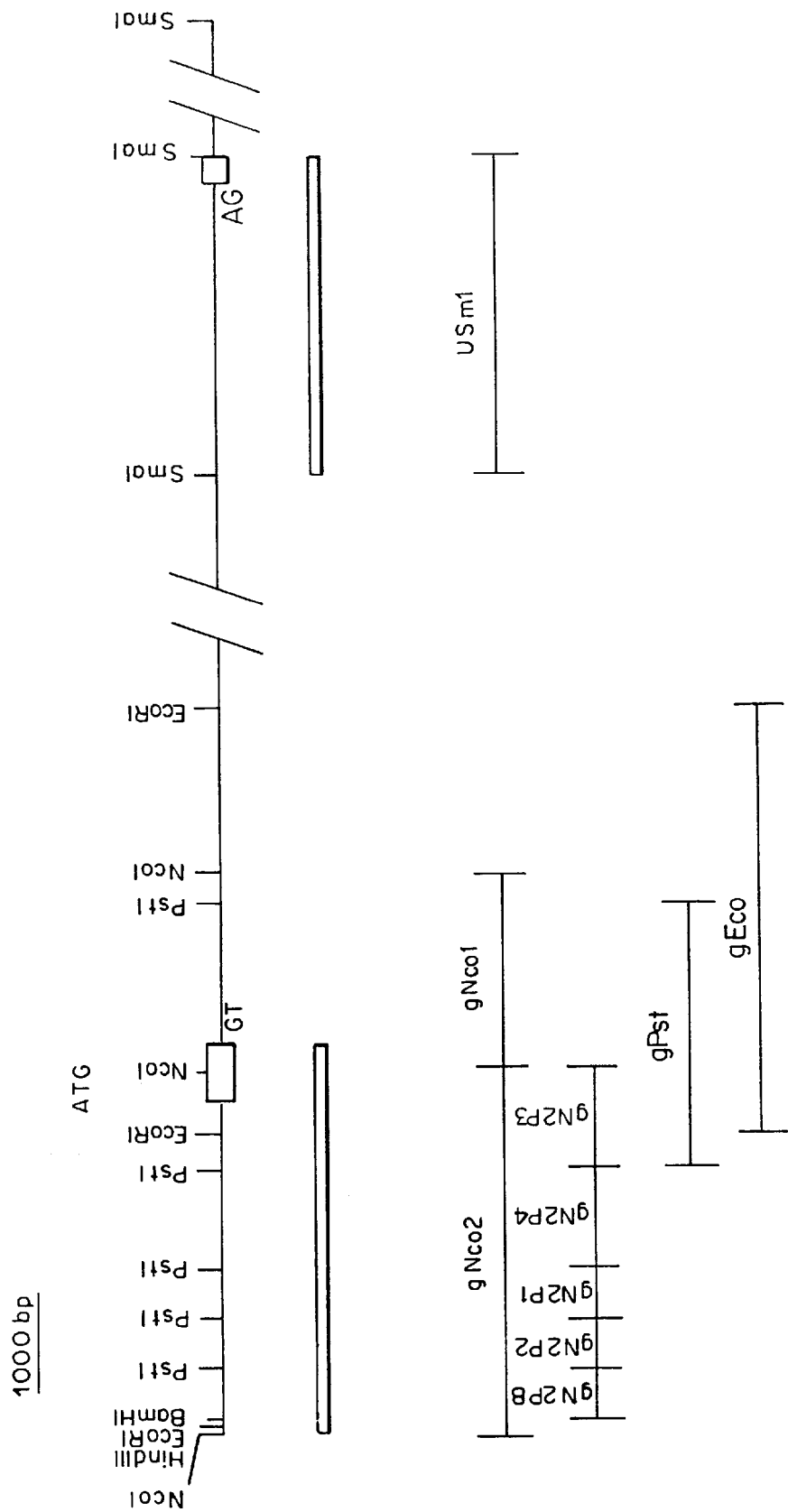
FIG. 1 shows, schematically, the partial restriction map and various pBluescript subclones of the 5' region, including the 5' upstream region, the first exon, the first intron and the second exon, of the human p75 TNF-R gene, as described in Example 1.

A human genomic library containing the human p75 TNF-R was obtained from Stratagene. This library was a phage library, from which 8 phages were positively identified as carrying the human p75 TNF-R gene, 6 of which phages were different. Various fragments from the positive phages were isolated, cloned and sequenced.

As is detailed herein below in the Examples, we have determined the sequence of the 5' region of the human p75 TNF receptor gene. We show that a 2 kb region 5' upstream of the published cDNA, as well as a region in the 3' part of the first intron contain promoter activity. There are reports of different mRNA sizes for the p75-R and it would seem that this results not only from different 3' ends but also from different 5' ends. The finding of promoter activity in the regions of the gene that we have sequenced is strong evidence that we have cloned at least one of the promoters for the human p75 TNF receptor gene. Primer extension analysis and RACE will show where the 5' end of the gene is, and what products of the p75 TNF-R gene are obtained when expression of this gene is controlled by the different promoter regions. A number of clones have been derived (as set forth in Examples 1 and 2) which encode the whole 5' upstream promoter region or parts thereof or the whole intron promoter region or parts thereof. The activity of the 5' upstream and intron promoter regions was demonstrated by inserting these regions into a vector encoding luciferase, and subsequently showing that these were capable of positively controlling the expression of the luciferase gene (Example 3).

Examination of the promoter sequences located in the 5' upstream region and in the first intron region of the p75 TNF-R gene (see Example 2 below) reveals a variety of sequence motifs which may allow response to transcription factors which are affected by inducing agents, including, for example, TATA boxes, CAP sites and consensus sequences for AP-2 and NF-κB (see also FIGS. 2A and 2B). These regulatory elements may allow for induced transient changes, superimposed on the pattern of constitutive expression of the receptor, perhaps by effects of certain cytokines which are formed at sites of inflammation.

Among the putative motifs discerned in the promoter regions (5' upstream and first intron regions), the following ones seem to be of particular interest: In the 5' upstream promoter region there are three canonical TATA boxes, two of which are followed very closely by CAP sites; three, closely located, and equaled spaced kappa-E2 motifs; four adjacent GC boxes; and binding motifs for several transcription factors which can mediate the effects of some inducing factors known to enhance p75 TNF-R expression, including NF-KB, the cytokine-2 motif and AP-2. In the first intron promoter region, particularly at the 3' end of the first intron there are, amongst others, a TATA box followed by a CAP site 25 bp. downstream and a threefold TCC repeat motif, which occurs twice in the p55 TNF-R promoter region.

Thus, it is assumed that the 5' upstream promoter region of the p75 TNF-R gene is the region necessary for the promoter activity of the p75 TNF-R gene, namely, to control the expression of the gene to ultimately result in the production of the normal p75 TNF-R receptor product, while the promoter region in the first intron is indicative that the p75 TNF-R gene encodes other forms of the receptor. Moreover, the promoter region in the first intron may also function as an enhancer element for the transcription of the p75 TNF-R gene. Furthermore, the promoter region in the first intron also contains a transcription inhibitory region upstream of the active intron promoter region, which inhibitory region may be involved in the modulation of expression of the other forms of the p75 TNF-R.

The present invention also concerns pharmaceutical compositions comprising a pharmaceutically acceptable carrier and a sequence motif or motif region of the invention. These compositions may be used against any disease caused by an excess of TNF, either endogenously present or exogenously administered. Examples of diseases are septic shock, graft-versus-host reactions, rheumatic diseases and other autoimmune diseases.

The way of administration can be via any of the accepted modes of administration for similar agents and will depend on the condition to be treated, e.g. intravenously, intramuscularly, subcutaneously, by local injection or by topical application, as the case may require.

The pharmaceutical compositions of the present invention are those designed for the introduction of the active ingredients, namely, the motif sequences, into the target cells of choice, i.e. those expressing the p75 TNF-R, the expression of which it is desired to control via control of its promoter, which control may be either an enhancement or an inhibition of the promoter activity. To introduce such motif sequences into cells, a number of procedures are known, for example:

(i) It is possible to construct by standard procedures a recombinant animal virus vector (e.g. derived from vaccinia) to whose DNA two genes will be introduced, one encoding a ligand that binds to cell-surface proteins expressed specifically by the target cells (e.g. in the case of CD4 lymphocytes and related leukemias, the AIDS gp120 protein binds specifically to these cells), and hence expression of this gene will target the virus specifically to the desired cells; and the second encoding the motif sequence, which will be introduced and subsequently expressed in these cells, via the virus.

(ii) It is possible to prepare an oligonucleotide sequence encoding the motif sequence which can be introduced to the cells in the form of an ointment (e.g. as is used for wart treatment where an oligonucleotide sequence is introduced into skin cells using an ointment formulation, which oligonucleotide blocks the wart-inducing agent, a papillovirus). It is possible to introduce the above oligonucleotide sequence into the cells using the above recombinant animal virus in which the second sequence carried by this virus will be the oligonucleotide sequence.

(iii) It is possible to employ the recently developed ribozyme approach. Ribozymes are catalytic RNA molecules that specifically cleave RNAS. Ribozymes may be engineered to cleave target RNAs of choice, e.g. the mRNAs encoding the new proteins and factors of the invention or encoding the motif sequences of the invention. Such ribozymes would have a sequence specific for the MRNA or motif sequence of choice and would be capable of interacting therewith (complementary binding) followed by cleavage of the mRNA or motif sequence, resulting in a decrease (or complete loss) in the expression of the protein it is desired to inhibit, or the motif sequence it is desired to inhibit, the level of decreased expression being dependent upon the level of ribozyme expression in the target cell. To introduce ribozymes, in the form of a pharmaceutical composition, into the cells of choice (e.g. those carrying the p75 TNF-R) any suitable vector may be used, e.g. plasmid, animal virus (retrovirus) vectors, that are usually used for this purpose (see also (i) above, where the virus has, as second sequence, a cDNA encoding the ribozyme sequence of choice). Moreover, ribozymes can be constructed which have multiple targets (multi-target ribozymes) that can be used, for example, to inhibit the expression of one or more of the proteins, or sequence motifs of the invention (For reviews, methods etc. concerning ribozymes see 65–73).

Thus, the pharmaceutical compositions may be those, comprising as active ingredient, the above noted recombinant animal virus, or they may be an ointment comprising an oligonucleotide encoding the motif sequence. The amount of active compound to be administered will depend on the route of administration, the disease to be treated and the condition of the patient.

The invention is illustrated by the following non-limiting examples:

Cell lines and culture conditions:

The baby hamster kidney (BHK) cells were grown and maintained in standard BHK cell-culture conditions (DMEM+10% FCS+2 mM glutamine).

EXAMPLE 1

Cloning and Analysis of clones containing the 5' region of the p75 TNF-R gene

Two human genomic libraries were screened (using standard hybridization methods) with the full-length cDNA encoding human p75 TNF-R (also known as TNF-RII). This cDNA contained the sequence from bases 90–1475 of the sequence according to Smith et al. (10). The following human genomic libraries in the form of recombinant phage libraries were employed: An ATCC library (ATCC No. 57738) specific for human chromosome 1; and a Stratagene human lymphocyte library (Stratagene No. 943202). Several screenings of the ATCC library did not reveal any positive phages, i.e. no phages containing a sequence hybridizable with the p75 TNF-R cDNA probe were contained in the library. Screening of the Stratagene library revealed 8 positive phages, 6 of which differed from each other as shown by restriction enzyme comparative analysis (results not shown).

Two of the above different positive phages, called U and H, were further examined by hybridization to different fragments of the p75 TNF-R cDNA: Both U and H hybridized to a 250 bp. fragment of the 5' end of the cDNA including the untranslated region (UTR), but did not hybridize to a somewhat shorter 160 bp. fragment cDNA, contained within the above 250 bp fragment at its extreme 5' end. A third phage, of the above different phages, called G, was isolated with the aforesaid 160 bp. fragment of the 5' region of the cDNA. Thus, G also encodes a 5' region of the p75 TNF-R gene.

Further characterization of the 3 phages (U, H, G) by hybridization to the 5' CDNA fragments (probes) revealed that: (i) with U and H, two SmaI restriction fragments, obtained from the p75 TNF-R sequence contained in these phages of sizes 1.9 and 3.6 kb, hybridized to the above noted 250 bp. CDNA probe; and (ii) with G, the above noted 160 bp. CDNA probe hybridized to two NcoI fragments, of sizes 2 and 1.1. kb, and also hybridized to a 2.4 kb EcoRI and a 1.5 kb PstI fragment, all of these NcoI, EcoRI and PstI fragments being obtained from the p75 TNF-R sequence contained in the phage G. All of the above fragments from phages U, H and G which hybridized to the 250 or 160 bp. cDNA probes were then subcloned into plasmids. Subcloning was by way of standard procedures using the plasmid pBluescript (Stratagene). Following subcloning, the various subcloned fragments of phages U, H and G were analyzed by restriction enzyme analysis to obtain a restriction map. In FIG. 1 there is shown, schematically, the restriction map (partial) of the plasmid clones which cover the 5' region of the human p75 TNF-R gene. It should be noted that the plasmids shown in FIG. 1 were derived from phage G (gNco1, gNco2, gPst, gEco, and the various subclones of gNco2 shown under gNco2), while the SmaI clone (USm1) was derived from phage U. In FIG. 1 the black bars indicate the regions that have been presently sequenced (i.e. from subclones gNco2, gNco1and USm1-see Example 2 below); the filled boxes indicate the regions of the known cDNA sequence of Smith et al. (10); and the exon/intron boundaries are indicated by "GT" (start of intron I/end of exon I) and "AG" (start of exon II/end of intron I).

In order to assure that the phages, of the above Stratagene library, represent the genomic organization of the p75 gene and are not the result of recombination, the following tests (or "check-ups") were performed:

(i) That the 1.9 kb SmaI fragment represents the genomic SmaI fragment can be shown indirectly by the fact that two independent phages (U and H) contain the same fragment which hybridizes to the 250 bp. cDNA probe.

(ii) To test whether the single phage isolate, G, of the very 5' region (i.e. extreme 5' end of the p75 TNF-R gene) represents the genomic organization, a comparison of the phage restriction pattern with the one of the native genomic DNA from U937 cells was made by digestion of the phage and genomic DNA with BamHI, EcoRI and PstI, followed by hybridizations with the 2 kb. NcoI fragment (from subclone gNco2). Comparison of the genomic and phage restriction patterns and hybridization of the restriction fragments to the 2 kb. NcoI fragment probe showed that both the phage and the genomic DNA had the same restriction pattern with the same fragments hybridizing to the probe (results not shown). Thus the single phage isolate, G, represents the actual genomic organization of the 5' region of the p75 TNF-R gene.

Moreover, from the above cloning, hybridization and restriction analysis, the following facts are revealed: a) by using the first part (90–1475 bp) of the published cDNA as a probe, 8 independent phages (6 of which differed from each other) can be isolated from the Stratagene library, each having an insert of about 15–20 kbp., this being indicative that the p75 TNF-R gene is rather large and is spread over several dozen kbp; and b) in view of the fact that phages U and H, while independent, did not contain the very 5' region of the p75 TNF-R gene, the first intron (intron I) is also rather long (>10 kb).

EXAMPLE 2

Sequence and characterization of the 5' region of the p75 TNF-R gene

To elucidate the structure of the 5' region of the p75 TNF-R gene, i.e. the location and nature of the promoter region, the various clones (subclones in pBluescript—see Example 1, above) were either partially or completely sequenced (see black bars in FIG. 1). In particular, clones gNco2 and USm1 were completely sequenced, while clones gNco1, gpst and gEco were partially sequenced. In FIG. 2 (A and B) there are shown, schematically, the sequences of the two parts of the 5' region of the p75 TNF-R gene that have been fully sequenced. Sequencing was by standard procedures in which the above clones in pBluescript were sequenced from both directions either with the Sequenase Version 2.0 kit (USB), or automatically with the Applied Biosystems Automated Sequencer (Model 737A DNA Sequencer, Applied Biosystems, USA). Following the sequencing, general sequence analysis was performed using the GCG (Genetics Computer Group, Madison, U.S.A., standard computer software package) package and specific sequence analysis, i.e. identification of transcription factor binding motifs, was carried out with the FINDPATTERNS option of the above standard software package. In FIG. 2A there is depicted the sequence of the very 5' region of the p75 TNF-R gene, including the first exon and exon/intron boundary (the first exon sequences and exon/intron boundary being determined by taking into consideration the cDNA sequence of Smith et al. (10)). The amino acid sequence (SEQ ID NO:2) of the cDNA is indicated above the nucleotide sequence. Underlined are four canonical TATA-boxes as well as other transcription factor binding sites (e.g. kappa-E2 sites and GC-boxes). The asterisk (*) indicates the start of the cDNA according to Smith et al. (10). In FIG. 2B there is depicted the sequence of the end of the first intron and part of the second exon (this also based on information from the Smith et al (10) cDNA sequence). Underlined are putative TATA-box, S1 nuclease hypersensitivity site (S1-HS), which is a TCC repeat, CAP-site, and various other putative transcription factor binding sites. The amino acid sequence (SEQ ID NO:4) of the cDNA is indicated above the nucleotide sequence (i.e. this is the start of the second exon).

The sequence analysis showed the following characteristic features of the 5' region of the p75-TNF-R gene:

(i) At the extreme 5' end of the p75-TNF-R gene (i.e. sequence of FIG. 2A, and indicated sequenced region of various subclones of phage G shown in FIG. 1 and described in Example 1): In this region a comparison of the cDNA sequence with our genomic 5' region clone showed that bases 1–166 of the cDNA sequence are identical to our sequence at same region, the 3' end of this region containing the coding sequence for amino acids 1–26, and continuously followed by the intron sequence with the characteristic GT dinucleotide consensus splice site at the 5' border of the intron. The aforesaid sequence is preceded by the 89 nucleotide long 5' untranslated region (UTR) of the published cDNA sequence (10). Since a similar UTR length has been described by another group for the p75-R cDNA (35) it is likely to correspond to the genuine size of the p75 TNF-R message. The first nucleotide in this UTR sequence, which may be the site of transcription initiation, is indicated with an asterisk. The sequence upstream of it contains three canonical TATA-boxes (at positions 1139, 1183 and 1431 of the sequence of FIG. 2A) and in addition, one unconventional TATA-box at position 1318. Two of the TATA-boxes, at positions 1318 and 1431, are followed by CAP-sites. However, in both cases, the distance between the CAP-site and the TATA-box is unusually small (5 bp). As to which one (or all) of the above TATA boxes is functionally active can be determined by standard analysis. No CCAAT-motif is present in the sequence. A sequence similar to the initiator-motif, shown to be involved in definition of the transcription start site (36), is located at position 1918 (YY1). Two, overlapping GC-boxes are present at positions 1938 and 1943 and two others, at positions 2082 and 2164 of the sequence of FIG. 2A. The two overlapping GC-boxes reside within a 22 bp. GC-stretch. Such long GC sequences have been proposed as binding sites for the transcription factor ETF (37, 38). At position 1566, there is a 31 bp. AT-rich sequence which can serve as an HMGI-binding motif. In certain promoters, such motifs have been demonstrated to contribute to promoter efficacy (39). A 3-fold repeat of the kappa E2 motif, which constitutes part of the enhancer of the immunoglobulin kappa light chain gene (40) is found at positions 1732, 1747 and 1762 of the sequence of FIG. 2A. The three repeats are very closely and equidistantly spaced by the same two hexanucleotides (AGGCCG).

Among the putative transcriptional factor binding motifs in the 5' flanking sequence, there are several which could confer response to agents which were shown to affect the expression of the p75-R. These include an NF-κB motif (32) at positions 130 (reverse), 194 (reverse) and 577 and a site homologous to the cytokine-1 motif (41) overlapping to the NK-κB motif at position 194, of the sequence of FIG. 2A. NF-κB sites can confer responsiveness to TNF and IL-1 (42), while the cytokine-1 motif binds TNF-induced factors. Both TNF and IL-1 have been shown to enhance the expression of the p75-R in certain cells (43, 44). A hexanucleotide which, in a repetitive form constitutes an interferon-responsive motif, AAGTGA (45) resides at positions 599 (reverse), 1356 (reverse) and 1616. A recently defined consensus sequence, the F6 consensus G A/G A A G C N G A A A G (SEQ ID NO:5) which binds an interferon-induced transcription factor, IRF-1 (46) is located at position 1982 (reverse). The consensus site for AP-2, T/C C G/C C C A/C N G/C G/C G/C (SEQ ID NO:6) (47) is found at position 1938, overlapping with the potential ETF site, and reverse copies of this element are located at positions 269, 874 and 1904 of the sequence of FIG. 2A. However, since this consensus sequence consists almost entirely of degenerate bases, its significance is uncertain. AP-2 is involved in the response to PMA as well as to cAMP (33). Both agents have been shown to induce the p75 TNF-R messenger (48, 49, 50). A sequence similar to the cAMP responsive element, TGAGTCA (51) occurs at position 1242, albeit with two mismatches. The p75 messenger was also reported to be induced upon T and B cell activation. In this process, Octamer binding factors (for B and T cells) (52, 53) and a factor binding the P sequence of the IL-4 promoter, CGAAAATTTCC (SEQ ID NO:7), (for T cells) (54) have been shown to play a role. A sequence similar to the octamer-motif occurs at position 918, ATGTAAAT and the P core sequence, AAATTTTT, at position 1222, of the sequence of FIG. 2A.

(ii) The intron sequence: This first intron has only been partially sequenced (see black bars in FIG. 1, the end of the sequence in FIG. 2A—i.e. starting from the GT dinucleotide, and then, separately, after a long (about 10 kb) unsequenced stretch, the entire sequence in FIG. 2B up to and including the AG dinucleotide, immediately before the indicated translated sequence).

Comparison of the cDNA with the sequence of the cloned 1,828 bp. genomic SmaI fragment (FIG. 2B) revealed that it contains at its very 3' end the continuation of the cDNA, again with the characteristic AG dinucleotide at the intron's 31 border, i.e. a 3' consensus splice site: $(C/U)_{11}NCAG$ (SEQ ID NO:8) (55), which precedes the coding sequence at position 1795 of the sequence of FIG. 2B, starting with Val27 in the leader of the p75 TNF-R. Therefore it is assumed that this sequence is part of the first intron of the p75 TNF-R gene. Surprisingly, within this intronic sequence (see underlined sites in FIG. 2B), we could define several sites or regions which are characteristic of promoters and cytokine inducibility: At position 630, there is a canonical TATA-box, which is followed, 26 bp. downstream, by a sequence similar to the initiator-binding site YY1, (36). Although no CCAAT-motif is discernible upstream of the TATA-box, an inverted copy of the element occurs at position 668 just downstream of the initiator motif. A TCC-repeat motif, found in various proto-oncogene and housekeeping-promoters, as well as twice in the pSS TNF-R promoter(56), occurs at positions 238 and 1310 (inverted), of the sequence of FIG. 2B.

Also, the intronic sequence contains consensus sites for transcription factors which may take part in regulation of p75-R expression. These include an NF-B consensus sequence (32) at position 255, two copies of a form of the cytokine-1 motif (which was also reported to respond to TNF) as it occurs in the human GM-CSF promoter (41), at positions 288 and 422, an interferon-responsive sequence, AAGTGA (45) (see above), at positions 388, 567 (reverse) and 757, a cytokine-2 element at position 709 (57), and three inverted copies of the AP-2 consensus sequence G G G / C C A / T G / C G /C C (SEQ ID NO:24) (47) at positions 359, 406 and 774. A consensus site for glucocorticoid receptor, AGAWCAGW (58) can be discerned at position 1025. This site may contribute to the reported upregulation of p75-R mRNA in the U937 cells by glucosteroids (59). A sequence which resembles the cAMP-responsive element TGACGTCA (51), but for two mismatches, can be found at positions 381 and 530.

The unexpected finding of promoter activity in an intron of the p75 TNF-R gene points to possible existence of additional translation products of this gene, besides the known form of the receptor. There are a number of ATGs downstream to the putative initiation binding motif in this sequence. The one occurring before the longest ORF (150 bp.) at position 874, is located within an almost perfect Kozak-box. The deduced 50 amino acid sequence starting at this point showed no similarity to any of the proteins found in Swiss-Protein data base (checked using the FASTA program [GCG, 1991—see ref. no. 60). At position 1768, close to the 31 end of the intron, there is an ATG start codon, in-frame with the receptor's coding sequence. The sequence surrounding this ATG does not fit very well to the consensus sequence proposed by Kozak (61) since it has a T in position −3, which occurs only in 1% of the 699 sequences analyzed by Kozak. However, also the translation start of the p75 TNF-R does not match precisely the consensus sequence, the C in its −3 position occurring only in 3% of the sequences. Translation starting at this "intronic" ATG would give rise to a truncated form of the receptor, in which the 26 N-terminal amino acids, which constitute a major part of the leader sequence of the described TNF-R, are replaced by 9 other residues, which may result in this protein product being an intracellular protein. It should also be noted that a protein known to be secreted may also exist in an intracellular form as was shown for the IL-1 receptor antagonist. Yet another possibility could be that translation of the MRNA starts at a Met within the cDNA part downstream of the SmaI clone, thus encoding a receptor which lacks, not only the leader sequence, but also part of the extracellular domain.

In any event, from the above analysis it seems likely that the promoter region within the intron sequence of the p75 TNF-R gene encodes two new protein products; a new protein and a new leader. However, our recent deletion analysis of the cloned first intron region, in particular the cloned approx. 1.9 kb intron region (see below, Example 3) revealed that upstream to the proposed new protein, there is no active promoter, and hence it is not apparent how such a new protein may be expressed. Accordingly, such a new protein encoded by a sequence (the observed ORF) within the first intron of the p75-TNF-R gene, is probably not expressed. The new leader sequence does however appear to be highly feasible in light of this recent deletion analysis, which shows that a strong promoter is present just upstream to the start of the leader.

The following is the sequence of this new leader, the nucleotide numbering corresponding to that shown in FIG. 2B.

NEW LEADER

1768/1

ATG GCA GTC TTC CCT TCT TCC TTC CAG GTG GCA TTT ACA CCC TAC Met ala val phe pro ser ser phe gln val ala phe thr pro tyr GCC CCG GAG CCC GGG (SEQ ID NO:9) ala pro glu pro gly (SEQ ID NO:10)

It should be noted that in the above sequence the sequence numbering starts with the nucleotide sequence number as in FIG. 2B and is followed by the amino acid sequence number, e.g. in first sequence (new leader) the nucleotide sequence is from 1768 to 1827 and amino acid sequence is 1–20.

Furthermore, it is also possible that the intron region promoter sequence, besides having the capability for controlling the expression of the above noted new leader product, may also function as an enhancer element for the transcription of the p75 TNF-R gene. Such downstream enhancers are well known in many eukaryotic genes.

Moreover, it has now been found (see Example 3 below) that the intron promoter region contains a transcription inhibitory region upstream of the active intron promoter, this inhibitory region possibly being involved in the modulation of expression of the p75 TNF-R gene, in particular, the expression of a new p75 TNF-R product which starts from the above new leader, that is a truncated form of the native p75 TNF-R.

To further clarify the above sequence analysis of the two promoter regions of the p75 TNF-R gene (the 5' upstream and the intron promoters), the following is a summary of the comparison of the sequences from clones G (5' upstream promoter region) and U (intron promoter region) and known sequence motifs, being indicated as "ref."

The motifs are presented in two groups: those found in the exact form reported by others ("no mismatch") and those that differ slightly (mismatch"). Thus for each motif, the following information is given: The name of the motif and its reported nucleotide sequence; and the related sequences which were found in the p75-R promoter sequences in accordance with the present invention.

The above information is presented in the following way:

(i) The phage in which we observed the related motif. G designates the phage clone in which 5' upstream promoter sequence was found (SEQ ID NO:1). U designates the phage clone in which the promoter sequence within the intron was found (SEQ ID NO:3);

(ii) The positions within the sequence with reference to SEQ ID NO:1 (clone G) and SEQ ID NO:3 (clone U) in which we observed the motif and the exact sequence of the motif; and iii) ref: reference to the publication in which the motif was defined (including the exact sequence thereof).

It should be noted that some of the motifs listed below are not described herein above and represent additional putative motifs of the 5' upstream and first intron promoters:

```
no mismatch insulin
insulin
                                GTGGAAA
G             537 : AACAT      GTGGAAA    CCAGG   (532-548 of SEQ ID NO:1)
ref :
insulin             0           GTGGAAA    Cell 45: 35-44 (1986)

AP-2
G :
AP-2_CS4                                   YCSCCMNSSS  (SEQ ID NO:6)
            1,938 : TGGCC      CCGCCCCGCC  CCGCC   (1,933-1,952 of SEQ ID NO:1)
            1,943 : CCGCC      CCGCCCCGCC  GCCTG   (1,938-1,957 of SEQ ID NO:1)

AP-2_CS4  / Rev                SSSNKGGSGR  (SEQ ID NO:11)
              269 : GTTGA      GGGTTGGGGG  TGCAG   (264-283 of SEQ ID NO:1)
              874 : AAGTG      GGGATGGGGG  GACAG   (869-888 of SEQ ID NO:1)
            1,904 : GGAGG      GGCGTGGGGG  AGGCG   (1,899-1,918 of SEQ ID NO:1)
            1,905 : GAGGG      GCGTGGGGGA  GGCGT   (1,900-1,919 of SEQ ID NO:1)

AP-2_CS5                       GSSWGSCC
              840 : CGCAG      GGCTGGCC    CTGTA   (835-852 of SEQ ID NO:1)
            1,335 : ACCTT      GGGAGGCC    AGAGG   (1,330-1,347 of SEQ ID NO:1)
            1,930 : AGGCC      GGCTGGCC    CCGCC   (1,925-1,942 of SEQ ID NO:1)
            1,953 : CCGCC      GCCTGGCC    TCTGG   (1,948-1,965 of SEQ ID NO:1)
AP-2_CS5  / Rev                GGSCWSSC
              839 : CCGCA      GGGCTGGCC   CCTGT   (834-851 of SEQ ID NO:1)
              856 : TATTA      GGGCTGGCC   ACTCA   (851-868 of SEQ ID NO:1)
U :
AP-2_CS4  / Rev                SSSNKGGSGR (SEQ ID NO:11)
            1,691 : AGACT      GGCAGGGGGA  GGGCC   (1,686-1,705 of SEQ ID NO:3)

AP-2_CS5  / Rev                GGSCWSSC
              359 : TTGTT      GGCCAGGC    TGGTC   (354-371 of SEQ ID NO:3)
              406 : GCTTC      GGCCTCCC    AAAGT   (401-418 of SEQ ID NO:3)
              774 : AGGGA      GGGCTCCC    AGGAG   (769-786 of SEQ ID NO:3)
ref :
AP-2_CS4       0   YCSCCMNSSS  (SEQ ID NO:6)   (33)
AP-2_CS5       0   GSSWGSCC    (47)

AP-3
G:
AP-3_CS                        TGTGGWWW
              536 : AAACA      TGTGGAAA    CCAGG   (531-548 of SEQ ID NO:1)
ref :
AP-3_CS        0   TGTGGWWW    Nucleic Acids Res. 20 : 3-26 (1992)

NF-kB
G :
NFkB_CS1                       GGGRHTYYHC  (SEQ ID NO:12)
              577 : GAGGT      GGGGTTTTCC  ATCCC   (572-591 of SEQ ID NO:1)
NFkB_CS1  / Rev                GDRRADYCCC  (SEQ ID NO:13)
              130 : AAGGG      GAGAAGCCCC  ATGTT   (125-144 of SEQ ID NO:1)
              194 : CCTGG      GAGGATCCCC  ACCTT   (189-208 of SEQ ID NO:1)
NFkB_CS4                       GGGRNTYYC
              577 : GAGGT      GGGGTTTTC   CATCC   (572-590 of SEQ ID NO:1)

U :
NFkB_CS1                       GGGRHTYYHC  (SEQ ID NO:14)
              255 : GTTCA      GGGGATTCTC  CTGCC   (250-269 of SEQ ID NO:3)
              256 : TTCAG      GGGATTCTCC  TGCCT   (251-270 of SEQ ID NO:3)

NFkB_CS4                       GGGRNTYYC
              256 : TTCAG      GGGATTCTC   CTGCC   (251-269 of SEQ ID NO:3)
```

-continued

```
NFkB_CS4 / Rev              GRRANYCCC
       1,460 : GTGCT  GAGAACCCC  CGTTC   (1,455-1,473 of SEQ ID NO:3)
ref :
NFkB_CS1     0  GGGRHTYYHC  (SEQ ID NO:12)  (32)
NFkB_CS4     0  GGGRNTYYC   Hematol Bluttransfus 32:411-415 (1989)

CK-2 (cytokine-2)
U :
CK-2                        TCAGGTA
         709 : CTGTC  TCAGGTA  GGGTC   (704-720 of SEQ ID NO:3)
ref :
CK-2         0  TCAGGTA  (57)

INF
G :
INF.1                       AAGTGA
       1,616 : TAAAT  AAGTGA  ATGAT   (1,611-1,626 of SEQ ID NO:1)
INF.1 /Rev                  TCACTT
         599 : GGGAG  TCACTT  CCCAG   (594-609 of SEQ ID NO:1)
       1,356 : GAAGA  TCACTT  GAGGG   (1,351-1,366 of SEQ ID NO:1)

U :
INF.1                       AAGTGA
         388 : ACCTC  AAGTGA  TCCAC   (383-398 of SEQ ID NO:3)
         757 : TGTGA  AAGTGA  TTTGC   (752-767 of SEQ ID NO:3)

INF.1 /Rev                  TCACTT
         567 : CTCTG  TCACTT  ACCAG   (562-577 of SEQ ID NO:3)
ref :
INF.1        0  AAGTGA  (45)
SP-1
G :
Sp1-ras1.3 /Rev             GCCCCGCCCC   (1,940-1,949 of SEQ ID NO:1)
       1,935 : GGCTG  GCCCCGCCCC  GCCCC   (1,930-1,949 of SEQ ID NO:1)
       1,940 : GCCCC  GCCCCGCCCC  GCCGC   (1,935-1,954 of SEQ ID NO:1)
ref :
Sp1-ras1.3   0  GGGGCGGGGC  (residues 1940-1949 of SEQ ID NO:1)
                            (SEQ ID NO:15)  Science 232:1410-3 (1986)

IL-6
G :
F6_CS /Rev                  STTTCNTTYC   (SEQ ID NO:16)
          18 : GTGCC  CTTTCCTTCC  CAAAC   (13-32 of SEQ ID NO:1)

IL-6_RE1 /Rev               TTCCCAG
         169 : ATTCG  TTCCCAG  GATGG   (164-180 of SEQ ID NO:1)
         553 : GTGAT  TTCCCAG  CCTCC   (548-564 of SEQ ID NO:1)
         603 : GTCAC  TTCCCAG  TTTCT   (598-614 of SEQ ID NO:1)
U :
IL-6_RE1                    CTGGGAA
          11 : GGGTC  CTGGGAA  GGCAC   (6-22 of SEQ ID NO:3)

IL-6_RE1 /Rev               TTCCCAG
       1,357 : AGGGC  TTCCCAG  AGGAG   (1,352-1,368 of SEQ ID NO:3)

;IL-6_RE1    0  CTGGGAA    MCB13, 1183 (93/FEB)
ref :
F6_CS        0  GRAANGAAAS  (SEQ ID NO:17)  (46)
;IL-6_RE1    0  ctgggaa    MCB13, 1183 (93/FEB)

oct2 (B cell development)
OCT 2                       ATGYAAAW
         918 : TCATG  ATGTAAAT  CCTGG   (913-930 of SEQ ID NO:1)
ref :
OCT 2        0  ATGYAAAW  (52)

GCRE (glucocorticoid receptor)
GCRE /Rev                   GAGTCA
          56 : CCCTG  GAGTCA  AGAAC   (51-66 of SEQ ID NO:1)
         596 : CCAGG  GAGTCA  CTTCC   (591-606 of SEQ ID NO:1)

U :
GCRE /Rev                   GAGTCA
       1,553 : CAGCA  GAGTCA  GTGCT   (1,548-1,563 of SEQ ID NO:3)
ref :
GCRE         0  TGACTC      Cell 43 : 177-88 (1985)
```

-continued

```
mismatch cAMP
1                            TGACGTCA
        1,242 : TCCTA   tgaggtca    GTTCA   mis=1   (1,237–1,254 of SEQ ID NO:1)
U :
1                            TGACGTCA
          371 : ACTCT   tgacctca    AGTGA   mis=1   (376–393 of SEQ ID NO:3)
          530 : AGCTG   tgaagtca    GACAG   mis=1   (525–542 of SEQ ID NO:3)
ref :
          cAMP_RE    0    TGACGTCA     (51)
NF-P (T cell development)
T-ACT /Rev                   AAATTTTcc
        1,222 : TCTTT   AAATTTTTAGAA    (1,217–1,233 of SEQ ID NO:1)

ref :
T-ACT              0    AAAATTTCC    (54)

Vitamin D (VDRE)
gnco2.seq x vdre         April 10, 1994     17:54. . . . .
        1,536   GCTATGGGTGAAAGAG   1,551   (SEQ ID NO:18)
            1   GCACTGGGTGAATGAG      16   (1–16 of SEQ ID NO:19)

ref :
VDRE       0    GCACTGGGTGAATGAGGACATTACTGAC       (SEQ ID NO:19)
                           J Cell Biochem 49 :37 p53
p53_RS                       AGGCATGCCT   (SEQ ID NO:20)
G       1,708 : GGGAC   agggaagcct    GTGGG   mis=2   (1,703–1,722 of SEQ ID NO:1)
p53_RS                       AGGCATGCCT   (SEQ ID NO:20)
U       1,573 : CCTGC   agacatgact    AGGGT   mis=2   (1,568–1,587 of SEQ ID NO:3)
U       1,736 : GCATC   aggcatggca    GAACC   mis=2   (1,731–1,750 of SEQ ID NO:3)
ref :
p53_RS     0    AGGCATGCCT    (SEQ ID NO:20)   Nature Genet 1: 45-9 (1992)

YY1 (initiator)
G :                          gtctccannnnnnnnng   (SEQ ID NO:21)
YY1     1,918 : GAGGC   gtgtccaaggccggctg   GCCCC   mis=1   (1,913–1,939 of
                                                                   SEQ ID NO:1)
U :                          gtctccannnnnnnnng   (SEQ ID NO:21)
YY1       656 : AAACC   GTCTCCATCTTCATTGG   GTGGT   (651–677 of SEQ ID NO:3)
ref :
YY1        0    gtctccannnnnnnnng   (SEQ ID NO:21)    (36)

CK-1
G :
1 /Rev                       GTGGAATCTC   (SEQ ID NO:22)
          360 : ACGAG   gtgacatctc    CCTCC   mis=2   (355–374 of SEQ ID NO:1)

U :
1 /Rev                       GTGGAATCTC   (SEQ ID NO:22)
          255 : GTTCA   ggggattctc    CTGCC   mis=2   (250–269 of SEQ ID NO:3)
ref :
CK-1       0    GAGATTCCAC    (SEQ ID NO:23)   (57)
```

EXAMPLE 3

Functional analysis—Promoter activity of the 5' region and the first intron region of the p75 TNF-R gene In order to gain first insight into the functional significance of some 5' regions of the p75 receptor gene, several regions were cloned into a vector carrying the luciferase reporter gene. The constructs were transfected into BHK cells, which in our hands proved to be the most convenient system for having a first idea about promoter activity. Even though our main interest was in the very 5' part of the p75-TNF-R gene, the finding of a putative TATA-box and CAP-site in the intron prompted us to test also this region in a functional assay.

For the functional assay of the promoter(s) of the p75 TNF-R gene the following procedure was performed: BHK cells were transfected by the calcium-phosphate method according to Sambrook et al. (31). In each experiment, 10 g of plasmid DNA was transfected to semi-confluent 6 cm dishes. After overnight (8–12 hrs) incubation, the cells were washed 3 times with PBS and supplemented with fresh medium. After further 24 hours incubation, cells were harvested and luciferase activity in lysate supernatants was determined, using a Lumitron Luminometer set on 10 sec integration (62). Values were calculated as relative light units (RLU). The various vectors encoding the luciferase gene had cloned into them different promoters to control expression of the luciferase gene as follows:

i) CMV: positive control (luciferase gene under control of the CMV-promoter); LUC-0: negative control (luciferase gene without regulating sequence); gBX: 5' region of p75-TNF-R gene (nt 1–2089 in FIG. 2A) without ATG in "sense" orientation; gBS: 5' region (nucleotide 1–2089 in FIG. 2A) without ATG in "antisense" orientation; UsBX: intron fragment (nt 1–1827 in FIG. 2B) in "sense" orientation; UsBH: intron fragment (nt 1–1827 in FIG. 2B) in "antisense" orientation; UBX: intron fragment (nt 1–869 in FIG. 2B)

without ATG in "sense" orientation; UBS: intron fragment (nt 1–869 in FIG. 2B) without ATG in "antisense" orientation.

It should be noted that the various putative promoter-carrying fragments (and control promoters and fragments), as noted above, were cloned into the promoter-less luciferase vector LUCO, which contains the luciferase gene (63) replacing the CAT gene in the expression vector pBL-CAT6 (64).

Figure 3:
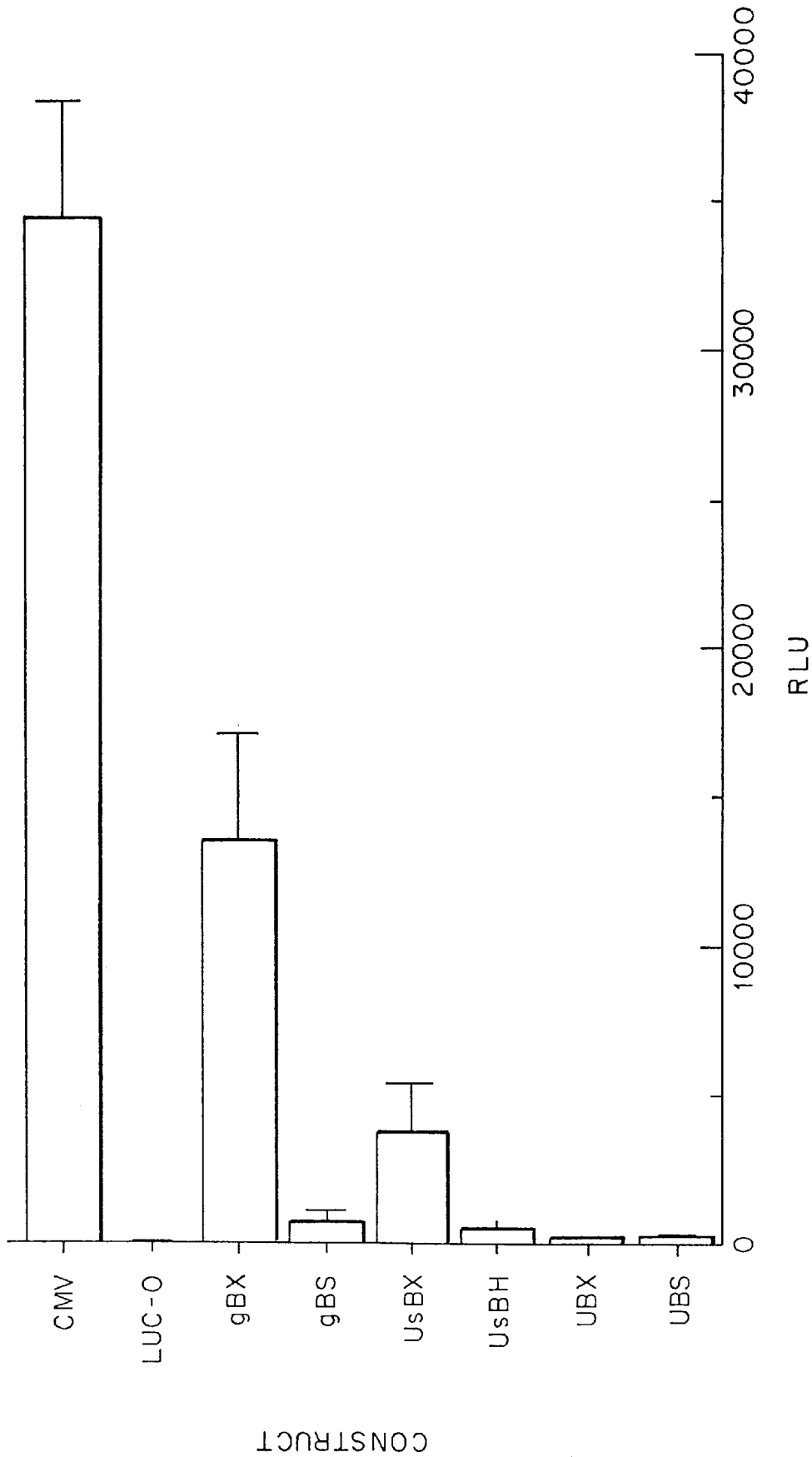
FIG. 3 shows, graphically, the results of determination of the activity of the 5' upstream and intron promoter regions as determined in an assay in which these promoter regions were used to control the expression (given in relative light units—RLU) of the luciferase gene in expression vectors encoding luciferase, as described in Example 3.

FIG. 3 shows the average results (standard deviation) of 3 independent transfections and subsequent luciferase assays. The very 5' region (gBX) shows very high activity compared with the positive control (CMV promoter). The promoter activity of this region is orientation dependent, as can be shown with the same fragment in antisense orientation (gBS) where a sharp drop in activity is observed. Interestingly, the intron region (UsBX) also shows significant promoter activity, here too the internal control in antisense orientation (UsBH) shows much less activity. This activity of the intron promoter is no longer detectable when only the part upstream of the first ATG (UBX or UBS) is linked to the luciferase gene, indicating that the observed promoter activity is mainly defined by the downstream part (i.e. that in UsBX in proper "sense" orientation). These two putative promoters will be analyzed further by standard procedures.

Deletion analysis of the 5' promoter region and first intron promoter region of the p75 TNF-R gene Deletional analysis of the promoter regions containing the 5' upstream promoter and the intron promoter were carried out to ascertain more precisely the sequence regions defining the active promoters. For this purpose, additional constructs were prepared, as detailed above, in which various deletion fragments of the 5' upstream promoter region and various deletion fragments of the 3' end of the first intron promoter region were inserted into the expression vectors carrying the luciferase reporter gene, and tested for promoter activity in the transfected BHK cells. The deletion fragments were generated by utilizing the above mentioned vectors containing the full-length 5' upstream promoter region and intron promoter region and then deleting from the 5' ends of these promoter regions, various portions to yield deletion fragments thereof, all by standard procedures. The functional assay of these deletion fragments for promoter activity was carried out as detailed above.

The deletion fragments of the 5' upstream promoter region included: (i) a fragment designated "GN2BX" extending from nucleotide no. 197 to nucleotide no. 2086 of the sequence of FIG. 2A; (ii) a fragment designated "75" extending from nucleotide no. 682 to nucleotide no. 2086 of the sequence of FIG. 2A; (iii) a fragment designated "PIII" extending from nucleotide no. 709 to nucleotide no. 2086 of the sequence of FIG. 2A; (iv) a fragment designated "76" extending from nucleotide no. 1335 to nucleotide no. 2086 of the sequence of FIG. 2A; and (v) a fragment designated "PI" extending from nucleotide no. 1527 to nucleotide no. 2086 of the sequence of FIG. 2A.

The deletion fragments of the intron promoter region included: (vi) a fragment designated "74" extending from nucleotide no. 872 to nucleotide no. 1827 of the sequence of FIG. 2B; and (vii) a fragment designated "UIIP" extending from nucleotide no. 1569 to nucleotide no. 1827 of the sequence of FIG. 2B.

All of the above deletion fragment (i)–(vii) were cloned into the expression vectors by standard methods and in a way that all were in the "sense" orientation.

From the results (not shown) it was apparent that:

(a) For the 5' upstream promoter region, the deletion fragments (i)–(iv), i.e. "GN2BX", "75", "PIII" and "76" all had full promoter activity, comparable to that of the non-deleted, cloned promoter region (nucleotides 1–2089 of FIG. 2A, see above), but however, the deletion fragment (v), i.e. "PI" had a very reduced promoter activity. (b) For the intron region promoter, the deletion fragment (vi), i.e. "74" showed very little promoter activity, this being comparable to the very low (if any) promoter activity of the cloned full-length fragment ("USBX", nucleotides 1–1827 of FIG. 2B) and of the other cloned fragment having only the 5' region of the intron promoter region (nucleotides 1–874 of FIG. 2B). However, the deletion fragment (vii), i.e. "UIIP" had a very significant increased promoter activity (comparable to those of "75", "PIII" and "76" noted above).

From the above results it may therefore be concluded that:

(a) For the 5' upstream promoter, the 5' end of the promoter is located between the 5' end of deletion fragment (iv) i.e. "76" (nucleotide no. 1335 of FIG. 2A) and the 51 end of deletion fragment no. (v) i.e. "PI" (nucleotide no. 1527 of FIG. 2A).

(b) For the first intron promoter region, there is only one promoter in the approx. 1.9 kb fragment, at the 3' end of the intron. The 5' end of this promoter is located between the 5' end of deletion fragment (vii) i.e. "UIIP" (nucleotide no. 1569 of FIG. 2B) and 1768 (start of new leader, see above). Moreover, the results also provided the surprising observation that there is an inhibitory region which is located between the 5' end of the full-length intron fragment (nucleotide 1 of FIG. 2B) and the 5' end of "UIIP" (nucleotide 1569 of FIG. 2B). At least part of this inhibitory region sequence is located between the 5' end of deletion fragment (vii) i.e. "74" (nucleotide 872 of FIG. 2B) and the 5' end of "UIIP" (nucleotide 1569 of FIG. 2B).

The 5' upstream promoter has thus now been more fully defined to be present within the region defined by nucleotides 1335 and 1527 of FIG. 2A.

For the intron promoter the results indicate that in the region between nucleotide 1 of FIG. 2B and the 5' end of "74" (nucleotide 872 of FIG. 2B) there is no promoter bur rather there exists a transcription inhibitory region. Further, this inhibitory region appears to extend into the "74" fragment up to the 5' end (nucleotide 1569 of FIG. 2B) of the smaller "UIIP" fragment.

Thus, the intron promoter region is from 5' end of "UIIP" (nucleotide 1569 of FIG. 2B to nucleotide 1768 of FIG. 2B), the start of the new leader.

This new intronic promoter is also unique in that besides being present in an intron it is also apparently devoid of a larger number of motifs usually present in promoters, all the observed motifs except for one TCC repeat (see above and FIG. 2B) being upstream in the region that is now believed to be inhibitory.

The existence of this promoter in the intron makes it likely that an alternative form of the p75-TNF-R is expressed, namely one having the presumed new leader sequence followed by the regions encoded by exons 2 and the remaining exons of the p75-TNF-R gene. This alternative form of p75 TNF-R is thus devoid of the region encoded by the first exon, namely the N-terminal part of the extracellular domain region which is known to be directly upstream of the cysteine-rich region (the TNF-binding region).

It is known in other proteins (e.g. dystrophin) that when the protein is transcribed from different promoters there occurs concurrently a mechanism of alternative splicing. Accordingly, it is possible that the putative new form of p75-TNF-R transcribed from the intronic promoter also undergoes alternative splicing to yield a final product which is a soluble form of p75-TNF-R that contains only the cysteine-rich domain; which is the TNF-binding region. This mechanism of alternative splicing of the p75 TNF-R transcript transcribed from the intronic promoter may be another way (besides the previously described protease cleavage process) in which the naturally-occurring soluble form of p75-TNF-R is produced.

The finding of the transcription inhibitory region in the intron upstream of the intronic promoter indicates the possibility that this inhibitory region serves as a modulator of the expression of the p75 TNF-R gene, and more particularly, of the putative new form of the p75-TNF-R. This modulation may be via the action of cytokines, in particular, TNF and IL-1, or differentiation-induced changes. Preliminary results (not shown) have indicated that, in fact, TNF is capable of enhancing the function of the intronic promoter by suppressing the inhibitory region. Further, there also appears to be cell-specific expression of the intronic promoter, some cells having naturally high expression of this promoter and others not, these differences being related to differentiation changes which have apparently led to the inactivation of the inhibitory region in some cell types.

Accordingly, the present invention also concerns the above inhibitory region.

EXAMPLE 4

Purification of transcription factors binding to the promoter region

Functional motifs in the promoter region (i.e. 5' upstream and first intron promoters) and the inhibitory region present in the first intron region upstream of the intron promoter (see Example 3) can be identified by step-wise deletion of nucleic acid sequence from the 3' and/or 5' end of the promoter and/or inhibitory regions by conventional means (Erase-a-Base kit, Promega Corp.). The deleted promoter or inhibitory region fragments are then tested for activity. Likewise, internal sequences can be deleted or changed by in vitro mutagenesis or linker scanning (31). Motifs that bind activating transcription factors are revealed by a loss of promoter activity when deleted or mutated. Conversely, motifs that bind transcription factors which suppress promoter activity are identified by mutated or deleted promoter fragments which have increased activity, compared to the wild-type promoter. Likewise, motifs concerned with activation or inhibition of the transcription inhibitory region can also be identified, which bind inhibitory factors or inhibition suppressor factors. A detailed analysis of these motifs is then carried out by chemical synthesis of oligonucleotides with the sequence of the original motif, and mutated forms of it. These oligonucleotides are linked to the promoter fragments lacking the corresponding motifs, and the resulting construct is tested for promoter activity. If the original activity is restored, the motif can be regarded as functionally unchanged, i.e. those mutations that have been introduced into the motif, do not interfere with its function. On the other hand, if less promoter activity is observed with a mutated motif, it can be concluded that the nucleotides which were changed compared to the wild-type motif, are essential for its function.

Thus, all of the various motifs set forth in Example 2 above, within the 5' upstream and intron promoter regions, can be subjected to the above analysis procedures to determine which are the fully functional ones.

Once a transcription factor binding motif has been identified, the corresponding transcription factor is isolated. For this purpose, extracts from several sources are screened for high expression of that transcription factor. The amount of transcription factor present can be measured by gel shift assays, using the above described oligonucleotides containing the sequence of the functional motif at 5'-end-labeled, ds-DNA probes.

Having identified an abundant source of the transcription factor, the conditions that are required for optimum binding can be defined. Different chemical parameters, such as pH, presence of various mono- and divalent cations, salt concentration and the presence of reducing agents, e.g. DTT or mercaptoethanol are adjusted to achieve this goal.

Having established optimal binding conditions for the transcription factor, purification is carried out by conventional means, e.g. by salt precipitation, phosphocellulose and/or DEAE chromatography. An enriched precipitation of the transcription factor is then purified further on a DNA affinity column, in which the oligonucleotide containing the corresponding motif is bound to an insoluble matrix, and the transcription factor-containing solution is passed over the column under conditions optimal for binding. After washing off contaminants, the purified transcription factor is eluted by conditions which do not allow DNA binding, e.g. pH shift, changed salt concentration, or chelation of divalent salts necessary for DNA binding (usually $Zn^{++}$).

Having purified the transcription factor allows the application of "reverse genetics" on that molecule: protein sequencing, cDNA cloning using degenerated oligonucleotides corresponding to protein sequence and finally, cloning of the gene encoding the transcription factor by screening genomic libraries using the CDNA as a probe.

Having all these tools: genomic clones, cDNA and purified transcription factors, allows to define ways to regulate the activity of the transcription factor by one of the following means: (1) influencing its promoter; (2) influencing its binding to the target in the p75 gene promoter; or (3) modulating its activity.

A detailed procedure for (1) is given in Example 5. Methods (2) and (3) can be achieved by screening a large number of drugs for interference with the function of this transcription factor.

In a similar fashion, an analogous procedure as detailed above may be carried out to identify, clone, characterize and regulate the activity of the factors which recognize the inhibitory region present in the first intron upstream of the intron promoter (see Example 3).

EXAMPLE 5

Modulation of promoter activity by specific sequence regions

The activity of a promoter can be regulated by scavenging transcription factors which are in short supply. This can be done by expressing multiple copies of the corresponding motifs to which the transcription factors bind. This mechanism has recently been demonstrated by Pai et al (34), who expressed and amplified the negative promoter domain of the c-myc promoter in the hamster CHO cell line. Following that, the authors observed increased expression of hamster c-myc and the corresponding changes in cell growth and morphology induced by myc protein. Much in the same way, it is possible to amplify promoter regions which activate and enhance promoter activity, and by that decrease the expression of the corresponding protein.

For the p75 promoter, either the whole extreme 5' region promoter or the whole promoter in the first intron (see Example 2), or parts thereof which have been identified as negative or positive regulatory domains, can be excised from the promoter sequence by restriction digest or exonuclease deletion of irrelevant sequences. The fragments obtained are then linked to a vector that allows gene amplification, and transfected into a cell line, e.g. CHO cells, which allows selection for amplified vector sequences. After selection and amplification, the obtained clones of CHO cells are checked for p75 gene expression on the mRNA and protein level. In addition, the function of the receptors in checked by cytotoxicity assay with TNF or with TNF mimicking antibodies as described in Israel Patent Application No. 103051.

Having established promoter regions which, upon amplification in this system, modulate the activity of the p75 receptor, these same regions are introduced into cells which do not allow selection for amplified gene products in two ways:

(1) Coexpression of promoter regions linked to a vector which contains a viral origin or replication (e.g. SV40 or EBNA), with a vector which expresses T antigen (of SV40), or EBNA antigen. This allows the replication of high numbers of episomal copies of the introduced promoter fragment in the nucleus of the target cell and thus mimics the effect of DNA amplification of integrated sequences.

(2) Chemical synthesis of a ds oligonucleotide comprising the promoter domain and application of sufficient amounts of that oligonucleotide to cells makes it likewise possible to scavenge the corresponding transcription factors and thus influence promoter activity. The chemistry of the oligonucleotides has to be changed in order to (a) make the oligonucleotide more lipophilic, so that it can pass the cytoplasmic membrane, and (b) enhance its stability in order to minimize degradation. This is done by conventional means, e.g. by using phosphothioate-coupled oligonucleotides.

REFERENCES

1. Tracey, J. T. et al. (1987) Nature 330:662–664.
2. Piquet, P. F. et al. (1987) J. Exp. Med. 166:1280–1289.
3. Beutler, B. and Cerami, C. (1987) NEJM, 316:379–385.
4. Hohmann, H.-P. et al. (1989) J. Biol. Chem. 264:14927–14934.
5. Engelmann, H. et al. (1990) J. Biol. Chem. 265:1531–1536.
6. Brockhause, M. et al. (1990) Proc. Natl. Acad. Sci. USA 87:3127–3131.
7. Loetscher, H. et al. (1990) Cell 61:351–359.
8. Schall, T. J. et al. (1990) Cell 61:361–370.
9. Nophar, Y. et al. (1990) EMBO J. 9:3269–3278.
10. Smith, C. A. et al. (1990) Science 248:1019–1023.
11. Heller, R. A. et al. (1990) Proc. Natl. Acad. Sci. USA 87:6151–6155.
12. Aggarwal, B. B. et al. (1985) Nature 318:665–667.
13. Israel, S. et al. (1986) Immunol. Lett. 12:217–224.
14. Tsujimoto, M. et al. (1986) Biochem. Biophys. Res. Commun. 137:1094–1100.
15. Ruggiero, V. J. et al. (1986) J. Immunol. 136:2445.
16. Holtman, H. and D. Wallach (1987) J. Immunol. 139:1161–1167.
17. Ding, A. H. et al. (1989) J. Biol. Chem. 264:3924.
18. Porteu, F. and Nathan, C. (1990) J. Exp. Med. 17:599–607.
19. Porteu, F. et al. (1991) J. Biol. Chem. 266:18846.
20. Ware, C. F. et al. (1991) J. Immunol. 147:4229.
21. Erikstein, B. K. et al. (1991) Eur. J. Immunol. 21:1033.
22. Winzen, R. et al. (1992) J. Immunol. 148:3454.
23. Espevik, T. et al. (1990) J. Exp. Med. 171:415–426.
24. Engelmann, H. et al. (1990) J. Biol. Chem. 265:14497–14504.
25. Thoma, B. et al. (1990) J. Exp. Med. 172:1019–1023.
26. Tartaglia, L. A. et al. (1991) Proc. Natl. Acad. Sci. USA 88:9292–9296.
27. Gehr, G. et al. (1992) J. Immunol. 149:911.
28. Heller, R. A. et al. (1992) Cell 70:47.
29. Brakebusch, C. et al. (1992) EMBO J. 11:943–950.
30. Vandenabeele, P. et al. (1992) J. Exp. Med. 176:1015.
31. Sambrook, J. et al. (1989) *Molecular Cloning: A Laboratory Manual,* Cold Spring Harbor Laboratory Press, Cold Spring Harbor, N.Y.
32. Lenardo, M. J. and Baltimore, D. (1989) Cell 58:227–229.
33. Imagawa, M. et al. (1987) Cell 51:251–260.
34. Pai et al. (1992) J. Biol. Chem. 267:12428–12431.
35. Kohno T. et al, (1990) Proc. Natl. Acad. Sci. USA, 87:8331–8335
36. Seto E. et al (1991) Nature 354:241–245
37. Kageyama R. et al. (1988) Proc. Natl. Acad. Sci. USA 85:217–224.
38. Kageyama R. et al. (1989) J. Biol. Chem. 264:15508–14.
39. Fashena S. J. et al. (1992) Mol. Cell Biol. 12:894–903.
40. Murre C. et al. (1989) Cell 56:777–83.
41. Shannon M. T. et al. (1990) Mol Cell Biol. 10:2950–2959.
42. Anisowicz A. et al. (1991) J. Immunol. 147:520–527.
43. Winzen R. et al. (1993) J. Immunol. 150:4346–53.
44. Kalthoff H. et al. (1993) J. Biol. Chem. 268:2762–6.
45. Fujita T. et al. (1987) Cell 49:357–67.
46. Harroch S. et al. (1993) J. Biol. Chem. 268:9092–9097.
47. Mitchell P. et al. (1987) Cell 50:847–61.
48. Scheurich P. et al. (1989) J. Exp. Med. 170:947–58.
49. Hohmann H-P. et al. (1990)—J. Biol. Chem. 265:22409–17.
50. Aggarwal B. B. et al. (1993) Lymph. Cyt. Res. 12:149–58.
51. Lewis E. et al. (1987) Proc. Natl. Acad. Sci. USA 84:3550–4.
52. Ullman K. S. et al. (1991) Science 254:558–62.
53. Corcoran L. M. et al. (1993) Genes Dev. 7:570–82.
54. Abe E. et al. (1992) Proc. Natl. Acad. Sci. USA 89:2864–8.
55. Aebi M. and Weismann C. (1987) TIG 3:102–107.
56. Kemper O. and Wallach, D. (1993) Gene 134:209–216.
57. Shannon M. F. et al. (1988) Proc. Natl. Acad. Sci. USA 85:674–678.

58. Okret S. et al. (1986) Proc. Natl. Acad. Sci. USA 83:5899–903.

59. Chambaut-Geurin, A-M. and Thomopoulos, P. (1991) Eur. Cyt. Netw. 2:355–60

60. GCG Computer Program, Genetics Computer Group, 575 Science Drive, Madison, Wis. USA 53711 (1991).

61. Kozak M. (1987) Nucleic Acids Res. 15:8125–8148.

62. Ausubel F. M. et al. (1989) Current Protocols in Molecular Biology, John Wiley, N.Y. 15.4.1

63. Nordeen S. K. (1988) Biotechniques 6:454–8.

64. Boshart K. et al. (1992) Gene 110:129–130.

65. Koizumi, M. et al. (1993) Biol. Pharm. Bull. (Japan) 16:879–83.

66. Crisell, P. et al. (1993) Nucleic Acids Res. 21:5251–5.

67. Barinaga, M. (1993) Science 262:1512–4.

68. Cantor, G. H. et al. (1993) Proc. Natl. Acad. Sci. USA 90:10932–6.

69. Shimayama, T. et al. (1993) Nucleic Acids Symp. Ser. 29:177–8.

70. Joseph, S. and Burke, J.M. (1993) J. Biol. Chem. 268:24515–8.

71. Chen, C. J. et al. (1992) Ann N.Y. Acad. Sci. 660:271–3.

72. Shore, S. K. et al. (1993) Oncogene 8:3183–8.

73. Zhao, J. J. and Pick, L. (1993) Nature 365: 448–51.

---

We claim:

1. An isolated and purified DNA molecule, comprising a promoter of the human p75 TNF-R gene having a sequence which is selected from the group consisting of a 5' upstream promoter sequence, contained within an approximately 2.0 Kbp NcoI fragment of a genomic clone of human p75 TNF-R, said fragment being located 5' upstream of the first exon and having a sequence comprising at least the sequence extending between nucleotides 1335 and 1527 of SEQ ID NO:1, and an intron promoter sequence located in the first intron between the first and second exons and contained within an approximately 1.9 Kbp SmaI fragment of a genomic clone of human p75 TNF-R, wherein said intron promoter sequence comprises at least the sequence extending between nucleotides 1569 and 1768 of SEQ ID NO:3.

2. The DNA molecule according to claim 1, wherein said intron promoter sequence comprises at least the sequence extending between nucleotides 1569 and 1827 of SEQ ID NO:3.

3. An isolated and purified DNA molecule containing a transcription inhibitory region that is located within the sequence of a 1.9 Kbp SmaI fragment of a genomic clone of human p75 TNF-R and upstream of an intron promoter sequence located in the first intron between the first and second exons, wherein said transcription inhibitory region has a sequence comprising the sequence extending between nucleotides 1 and 1569 of SEQ ID NO:3.

4. A composition, comprising the DNA molecule according to claim 3 and a carrier.

* * * * *

SEQUENCE LISTING (1) GENERAL INFORMATION:

(iii) NUMBER OF SEQUENCES: 24

(2) INFORMATION FOR SEQ ID NO: 1:

(i) SEQUENCE CHARACTERISTICS:
        (A) LENGTH: 2181 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION:2094..2171

(xi) SEQUENCE DESCRIPTION: SEQ ID NO: 1:

```
CCATGGAACA CTGTGCCCTT TCCTTCCCAA ACCCTCACCC CTGGGCCTGA CCCTGGAGTC     60

AAGAACTGCA CTTGGCAGAG TTCAGAGAGA AGTCGCCTGC TCTCAAGCCT GGGTCGGCCT    120

GGAGAAGGGG AGAAGCCCCA TGTTGCATAG AGATTAAGCT TGAATTCGTT CCCAGGATGG    180

GACCTAAGCC TGGGAGGATC CCCACCTTCA GGAGGTGATG GTGCCATTCA CTGGGATAGG    240

GAAACTGGCA GGAGGAGCCG GTTGTTGAGG GTTGGGGGTG CAGACAGTCT GTTGGTCCCA    300

TTGGTCTTGA GGTGTGTGGG GGACAACTAG AGAGAACTAT TGTCCCCTGC TTCCACGAGG    360

TGACATCTCC CTCCTGCCTT CAGCTCTATT TTAGGGATCA AGGAGTCCTT GGAGCTGCTC    420

CTAGGCATTC TCATAAGGGC CAGAAGAGCT CTGCATGTCT GTCCAGCGGC TCTGCAGAGT    480

TAAGGCTGTG GGTCATACCA GCCACACCCT CAGCGTGGTC CATGTCACAG AAACATGTGG    540

AAACCAGGTG ATTTCCCAGC CTCCTGGTCA GGAGGTGGGG TTTTCCATCC CCAGGGAGTC    600

ACTTCCCAGT TTCTCACTCA GCACTCAGCA CCTAGAAGCA CCATCCTTGC AGGCTCCACT    660

GTGGGGCTGG TGGCCGGGAG AAAGGGTCTC TGTACCTCTT CAGGCAGCCT GCAGTGAGGA    720

AACAGGGAAC AGAATAGCCT CCTGCCACCC AGCCCACCCC AACCCTTAGA AATGCCCTAT    780

GTGCTGGGGG CTAGGACCCC CGTAATCCAG GGCTGGAGGA ATGTGCTCTG GCCCCGCAGG    840

GCTGGCCCTG TATTAGGGCT GGCACTCAAA GTGGGGATGG GGGACAGAT TGCAGCTGGA    900

ATGGGTGCTC GGTCATGATG TAAATCCTGG GGAAGCCAGC TCTCCTGGGC CTGGTCTCAG    960

CAGCCCCTCA GGGGCCTGCA GCTTCCCTGG TGACATTCTC TCCCAGCCTC TGTTCATCTG   1020

CCCCCTGCCT GGGCAGGAGA CTTGAGCAGG GAAGTGCAGA GTCTTCTCCC TGTGAGAAGG   1080

CTGGATGCGT GTTTAAGGAT AAATGAACAC GCGAAGAGTA GTAACAACAG CCAAGATTTA   1140
```

```
TAAATGCCTA TTGTTATATA TGTAGATACT TACTTAAGTA TATATAAAGT ACAGACTGCA    1200

TTATGTATAT TACATATCTT TAAATTTTTA GAATAGTCCT ATGAGGTCAG TTCAGAGATC    1260

CAGACCCAGG TGGTCTGGCT CTAGAGTCTA AACAGGCCGA GTGCAGTGGC TCACACCTAT    1320

AATCCCAGCA CCTTGGGAGG CCAGAGGCGG GAAGATCACT TGAGGGTGGG AAGAACACGT    1380

GAGCTCAGGA GTTCGAGACC AGCCTGGACA ACATGGCGAA ACCCCATCTC TATAAAGAAA    1440

TCAGCCTAGC ATGGTGGCCC GAGCCTGTAG TCCCAGCTAC TCGGGAGGCT GAGGTGGGAG    1500

GATCGCTTGA GCGCAGGAGT TGGAGGCTGC AGTGAGCTAT GGGTGAAAGA GTGAGACCTT    1560

GTCTCAAAAA AAATTAAAAA ATAAGAATTA AATATATTTA AAATAGAGTC TAAATAAGTG    1620

AATGATCTAG AATTCTCTTG GTTCCCCTAA AGCAGCTGTC AGCTTTGGGG GATGTTTTTC    1680

CAAATTAGTG CCTCACCCTC ACGGGACAGG GAAGCCTGTG GGAGCTGGGA GGGCAGGTGG    1740

AGGCCGGGCA GGTGGAGGCC GGGCAGGTGG AGATGGTGAT TCGAAGAGGA GGGGACGATA    1800

GGAGGAGGTT GAGGGGTCAC CCGAGTGCTG GGAGTGACGC TGGAGGTATC GGCCCAGCGA    1860

TGCTGGAGTG GTCGGGTCGG AGGCCCAGCA GCGTCTGGGG AGGGGCGTGG GGGAGGCGTG    1920

TCCAAGGCCG GCTGGCCCCG CCCCGCCCCG CCGCCTGGCC TCTGGCCCGC TGGGGCGCGG    1980

GCTTTCGCTT TCAGTCGAGG GCTAGCGAGC GCAGCGGAGC CTGGAGAGAA GGCGCTGGGC    2040

TGCGAGGGCG CGAGGGCGCG AGGGCAGGGG GCAACCGGAC CCCGCCCGCA CCC ATG       2096
                                                            Met
                                                             1

GCG CCC GTC GCC GTC TGG GCC GCG CTG GCC GTC GGA CTG GAG CTC TGG     2144
Ala Pro Val Ala Val Trp Ala Ala Leu Ala Val Gly Leu Glu Leu Trp
         5                   10                  15

GCT GCG GCG CAC GCC TTG CCC GCC CAG GTGGGTGACT                       2181
Ala Ala Ala His Ala Leu Pro Ala Gln
         20                  25

(2) INFORMATION FOR SEQ ID NO: 2:

(i) SEQUENCE CHARACTERISTICS:
        (A) LENGTH: 26 amino acids
        (B) TYPE: amino acid
        (D) TOPOLOGY: linear (ii) MOLECULE TYPE: protein (xi) SEQUENCE DESCRIPTION: SEQ ID NO: 2:

Met Ala Pro Val Ala Val Trp Ala Ala Leu Ala Val Gly Leu Glu Leu
 1               5                  10                  15

Trp Ala Ala Ala His Ala Leu Pro Ala Gln
             20                  25

(2) INFORMATION FOR SEQ ID NO: 3:

(i) SEQUENCE CHARACTERISTICS:
        (A) LENGTH: 1827 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION:1795..1827

(xi) SEQUENCE DESCRIPTION: SEQ ID NO: 3:

CCCGGGGGTC CTGGGAAGGC ACAATGGTGA CAGTGCTGCA GCTCTGCACT CCTGGAGGGT    60
```

```
CACTCAGAGA CCCGAGAGAG GAGGGCTCTG CGTCTGCTCC TCTGTCCAGG GCTGTAGCTT      120

CTCTGGGTGC CTTTGCTTTT CTCTTTTCTC CCCTCTTTTT TTTTTTTTTT CGAGATGGAG      180

TTTTGCTCTG TCAATTAGGC TGGAAGTGCA GTGGCATGAT CTCAGCTCAC TGCAACCTCC      240

TCCTCCCAGG TTCAGGGGAT TCTCCTGCCT CAGCCTCCAG AGTAGCTGGG ATTACAGGCA      300

CACGCCACTA TGCCGGGATA ATTTTGTATT TTTAGTAGAG ACAGGGTTTT GCCTTGTTGG      360

CCAGGCTGGT CTCGAACTCT TGACCTCAAG TGATCCACCT GCTTCGGCCT CCCAAAGTGC      420

TGGGATTACA GGTGTGAGCC ACCACACCTG GCCCTCTCTC TCTTTTCATT CATCACATTG      480

TTCATCTCTT CCCGGAGGCA TCCAGCACAG TCTTTGAGAC TGTGAGCTGT GAAGTCAGAC      540

AGGACCCAGG TCCAAACCCT TCTCTGTCAC TTACCAGGTC TGGGACCTTG GGCAGGTGAC      600

CTGCCCTCTC AGGCCTCGGT TTCCTGTTCT ATAAAATGGC TGCAGTAGGG AAACCGTCTC      660

CATCTTCATT GGGTGGTTGG GAAGTCTTGC TGAGACCACA CACCTGTCTC AGGTAGGGTC      720

TTCCAGAAGC AGAGCCTGAG GCAGGGATCT TTGTGAAAGT GATTTGCTAG GGAGGGCTCC      780

CAGGAGAAGC AGGCAGGGCA GGTCAGGGGA GGGGGCTTAG CAGGGACGTT GTTCACCAGC      840

TTCAGCCCAA CACCACGGGG GTGGCTCTGG ACCATGAATT GTACCAGGGT GGGTCCCACC      900

TTGAGGCTGT GGAGCATTCA TTATCAGCCA ACACCCACAG CAGCTGGGGG AGCGGTGCCC      960

TGCTGGCAGC AGGGGTCTGA GTGGGGTGCA ACAGCACCCA CCAATTCGAG CAGCAGAAAC     1020

GCTTAGAACA GTGCCTGGTA CCTAGGCAGT GCTTCAAAAA TGGCAACGAT TGTCATGGTC     1080

ATAACCAACA TTCAGCTGAT GAGTGCCGGC TCTACGGTGG GTCCCATGTG AGAGATTGAG     1140

GGTCTAGAGA TGACAAGGCT GCCACCTCTG CTGTCTGCAT CACAAGTGTG TGTGTACACA     1200

TGTGTGTGCA TACATACCCA CAGGGGGTGG AACGACAAGC AAGTAACCAT TCCAGAACAA     1260

TGAGATGACT GTTAGAGGGG TCATAACCCA CGTTTAGAGA GAGCCGAGAG GAGGAGGAGG     1320

AGGAGCTTGA ATTAGCCTTG GGTAGTCAGG GAGGGCTTCC CAGAGGAGGC AGCACTCATC     1380

TTGAAAGACA AAGGGATGTT TCAGGTGCAG GAGGGAAGGA GAGGTATCTT CCTTCCTCAG     1440

CAGAAGGCAG CTTTGTGCTG AGAACCCCCG TTCTCTGTGA CCAAGGCCAC TGTCTTCTGG     1500

ATATCTGTCC CATGCAGTGT TAGGGGTCAC CCAGCACTGG AGAAGGCCAG CAGAGTCAGT     1560

GCTTCTGCCT GCAGACATGA CTAGGGTACA CTGAGGTGGG GAGGCAGGGG AGGTAAAAGA     1620

AGGCACGAGC TCTCCTTCCT GTACCCTGCT CCAGGGGGAG AAACCTCCCC AGCCATCATC     1680

AGTGCAGACT GGCAGGGGGA GGGCCAAACA TTTGCAGGGC GGGGACCTGG GCATCAGGCA     1740

TGGCAGAACC CAGGGGCGGC CCTGTTGATG GCAGTCTTCC CTTCTTCCTT CCAG GTG      1797
                                                                Val

GCA TTT ACA CCC TAC GCC CCG GAG CCC GGG                              1827
Ala Phe Thr Pro Tyr Ala Pro Glu Pro Gly
        30                  35

(2) INFORMATION FOR SEQ ID NO: 4:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO: 4:

Val Ala Phe Thr Pro Tyr Ala Pro Glu Pro Gly
 1               5                  10
```

(2) INFORMATION FOR SEQ ID NO: 5:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

```
GRAAGCNGAA AG                                                12
```

(2) INFORMATION FOR SEQ ID NO: 6:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

```
YCSCCMNSSS                                                   10
```

(2) INFORMATION FOR SEQ ID NO: 7:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

```
CGAAAATTTC C                                                 11
```

(2) INFORMATION FOR SEQ ID NO: 8:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

```
YYYYYYYYYY YNCAG                                             15
```

(2) INFORMATION FOR SEQ ID NO: 9:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION:1..60

(xi) SEQUENCE DESCRIPTION: SEQ ID NO: 9:

```
ATG GCA GTC TTC CCT TCT TCC TTC CAG GTG GCA TTT ACA CCC TAC GCC      48
Met Ala Val Phe Pro Ser Ser Phe Gln Val Ala Phe Thr Pro Tyr Ala
         15                  20                  25
```

```
CCG GAG CCC GGG                                              60
Pro Glu Pro Gly
        30
```

(2) INFORMATION FOR SEQ ID NO: 10:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO: 10:

```
Met Ala Val Phe Pro Ser Ser Phe Gln Val Ala Phe Thr Pro Tyr Ala
 1               5                  10                  15

Pro Glu Pro Gly
        20
```

(2) INFORMATION FOR SEQ ID NO: 11:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

```
SSSNKGGSGR                                                   10
```

(2) INFORMATION FOR SEQ ID NO: 12:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

```
GGGRHTYYHC                                                   10
```

(2) INFORMATION FOR SEQ ID NO: 13:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

```
GDRRADYCCC                                                   10
```

(2) INFORMATION FOR SEQ ID NO: 14:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 14:

```
GGGRHTYYHC                                                                 10

(2) INFORMATION FOR SEQ ID NO: 15:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 15:

GGGGCGGGGC                                                                 10

(2) INFORMATION FOR SEQ ID NO: 16:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 16:

STTTCNTTYC                                                                 10

(2) INFORMATION FOR SEQ ID NO: 17:

(i) SEQUENCE CHARACTERISTICS:
          (A) LENGTH: 10 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 17:

GRAANGAAAS                                                                 10

(2) INFORMATION FOR SEQ ID NO: 18:

(i) SEQUENCE CHARACTERISTICS:
          (A) LENGTH: 16 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 18:

GCTATGGGTG AAAGAG                                                          16

(2) INFORMATION FOR SEQ ID NO: 19:

(i) SEQUENCE CHARACTERISTICS:
          (A) LENGTH: 28 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO: 19:

GCACTGGGTG AATGAGGACA TTACTGAC                                             28

(2) INFORMATION FOR SEQ ID NO: 20:
```

```
    (i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO: 20:

AGGCATGCCT                                                                 10

(2) INFORMATION FOR SEQ ID NO: 21:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO: 21:

GTCTCCANNN NNNNNNG                                                         17

(2) INFORMATION FOR SEQ ID NO: 22:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO: 22:

GTGGAATCTC                                                                 10

(2) INFORMATION FOR SEQ ID NO: 23:

(i) SEQUENCE CHARACTERISTICS:
         (A) LENGTH: 10 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO: 23:

GAGATTCCAC                                                                 10

(2) INFORMATION FOR SEQ ID NO: 24:

(i) SEQUENCE CHARACTERISTICS:
         (A) LENGTH: 12 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO: 24:

GGGCCATGCG CC                                                              12
```